United States Patent [19]
Cappello et al.

[11] Patent Number: 6,036,958
[45] Date of Patent: Mar. 14, 2000

[54] TSETSE THROMBIN INHIBITOR

[75] Inventors: Michael Cappello, New Haven; Serap Aksoy, Woodbridge, both of Conn.

[73] Assignee: Yale University, New Haven, Conn.

[21] Appl. No.: 09/180,605

[22] PCT Filed: May 9, 1997

[86] PCT No.: PCT/US97/07968

§ 371 Date: Jul. 15, 1999

§ 102(e) Date: Jul. 15, 1999

[87] PCT Pub. No.: WO97/43309

PCT Pub. Date: Nov. 20, 1997

Related U.S. Application Data

[60] Provisional application No. 60/017,235, May 10, 1996.

[51] Int. Cl.[7] .......................... A61K 39/00; A61K 38/57; C07K 14/81
[52] U.S. Cl. .......................... 424/185.1; 514/12; 530/324
[58] Field of Search .............................. 424/185.1, 191.1; 514/12; 530/324

[56] References Cited

PUBLICATIONS

Cupp et al. (1998) Blood-feeding strategy of *Haematobia irritans* (Diptera: Muscidae), Journal of Medical Entomology, vol. 35(4), pp. 591–595.

Ribeiro et al. (1994) Salivary vasodilators of *Aedes triseriatus* and *Anopheles gambiae* (Diptera: Culicidae). Journal of Medical Entomology, vol. 31(5), pp. 747–753.

Cappello, M., et al., "Isolation and Characterization of Tsetse Thrombin Inhibitor" Am. J. Trop. Med. Hyg. 54: 475–480 (1996).

Cappello, M., et al., Tsetse Trhombin Inhibitor: Bloodmeal–Induced Expression Proc. Nat. Acad. Sci. USA 95: 14290–14295 (1998).

Mant, M.J. & Parker, K.R., "Two Platelet Aggregation Inhibitors in Tsetse Saliva" Brit. J. Haematology 48: 601–608 (1981).

Parker, K.R., & Mant, M.J., "Effects of Tsetse Salivary Gland Homogenates on Coagulation" Thrombos. Haemostas. 42:743–750 (1979).

*Primary Examiner*—Elizabeth Slobodyansky
*Attorney, Agent, or Firm*—Mary M. Krinsky

[57] ABSTRACT

A potent and specific inhibitor of thrombin is purified from salivary gland extracts of the tsetse fly, *Glossina morsitans morsitans*. The inhibitor has a molecular weight of 3530 Daltons as determined by laser desorption mass spectroscopy. The inhibitor is useful as an anticoagulant and an inhibitor of platelet aggregation and in pharmaceutical and immunogenic compositions.

14 Claims, 4 Drawing Sheets

```
GCACGAGGTACTATTTTTCTTGCTCAGCATTATTTATCTGATAGTTGCCGCACCTGGTGAACCAGGTGCACCCATAGATT
├────┼────┼────┼────┼────┼────┼────┼────┼────┼────┼────┼────┼────┼────┼────┼────┤ 80
CGTGCTCCATGATAAAAAGAACGAGTCGTAATAAATAGACTATCAACGGCGTGGACCACTTGGTCCACGTGGGTATCTAA

Ala Arg Gly Thr Ile Phe Leu Ala Gln His Tyr Leu Ser Asp Ser Cys Arg Thr Trp  •  Thr Arg Cys Thr His Arg Leu
    His Glu Val Leu Phe Phe Leu Leu Ser Ile Ile Tyr Leu Ile Val Ala Ala Pro Gly Glu Pro Gly Ala Pro Ile Asp
  Ser Thr Arg Tyr Tyr Phe Ser Cys Ser Ala Leu Phe Ile  •   •  Leu Pro His Leu Val Asn Gln Val His Pro  •  Ile

ATGACGAATACGGGGATAGCAGCGAAGAAGTTGGTGGCACACCTTTGCATGAGATTCCTGGCATAAGGCTTTAATTTAGT
├────┼────┼────┼────┼────┼────┼────┼────┼────┼────┼────┼────┼────┼────┼────┼────┤ 16
TACTGCTTATGCCCCTATCGTCGCTTCTTCAACCACCGTGTGGAAACGTACTCTAAGGACCGTATTCCGAAATTAAATCA

•  Arg Ile Arg Gly  •  Gln Arg Arg Ser Trp Trp His Thr Phe Ala  •  Asp Ser Trp His Lys Ala Leu Ile  •
  Tyr Asp Glu Tyr Gly Asp Ser Ser Glu Glu Val Gly Gly Thr Pro Leu His Glu Ile Pro Gly Ile Arg Leu  •  Phe Ser
    Met Thr Asn Thr Gly Ile Ala Ala Lys Lys Leu Val Ala His Leu Cys Met Arg Phe Leu Ala  •  Gly Phe Asn Leu Val

ACCAGAAGAAGAATTGATTAAGATCAGTTCGTCCGAATTTGTAAAGTTCGAAGAAATAAATGCATAAAAAAGAATAATAT
├────┼────┼────┼────┼────┼────┼────┼────┼────┼────┼────┼────┼────┼────┼────┼────┤ 24
TGGTCTTCTTCTTAACTAATTCTAGTCAAGCAGGCTTAAACATTTCAAGCTTCTTTATTTACGTATTTTTTCTTATTATA

Tyr Gln Lys Lys Asn  •  Leu Arg Ser Val Arg Pro Asn Leu  •  Ser Ser Lys Lys  •  Met His Lys Lys Glu  •  Tyr
    Thr Arg Arg Arg Ile Asp  •  Asp Gln Phe Val Arg Ile Cys Lys Val Arg Arg Asn Lys Cys Ile Lys Lys Asn Asn Ile
      Pro Glu Glu Glu Leu Ile Lys Ile Ser Ser Ser Glu Phe Val Lys Phe Glu Glu Ile Asn Ala  •  Lys Arg Ile Ile

TGATGCAACTAAAAAAAAAAAAAAAAAAA
├────┼────┼────────────────▶ 269
ACTACGTTGATTTTTTTTTTTTTTTTTTT

•  Cys Asn  •  Lys Lys Lys Lys Lys Lys
    Asp Ala Thr Lys Lys Lys Lys Lys Lys
  Leu Met Gln Leu Lys Lys Lys Lys Lys Lys
  ─────────────────────────────▶
```

Figure 4

TSETSE THROMBIN INHIBITOR

RELATED APPLICATION DATA

This application is a 371 of PCT/US97/07968 filed May 9, 1997 which claims the benefit of U.S. Provisional Application Ser. No. 60/017,235 filed May 10, 1996.

TECHNICAL FIELD

This invention relates to an inhibitor of thrombin isolated and purified from tsetse flies.

BACKGROUND OF THE INVENTION

Hematophagous arthropods have evolved a variety of strategies to facilitate the taking of a blood meal from their vertebrate hosts. Central to the success of these bloodfeeders is their ability to effectively interfere with host coagulation, thereby allowing for rapid and uninterrupted ingestion of blood from lacerated vessels in the epidermis. To this end, many bloodfeeding species, including ticks[1,2] sandflies[3], redivided bugs[4,5] blackflies[6] and mosquitoes[7,8], produce potent antihemostatic substances, which include anticoagulants, anti-platelet agents, and vasodilators.

Tsetse flies are an important vector of African trypanosomiasis, or sleeping sickness, a devastating disease of humans caused by infection with the hemoflagellate protozoa *Trypanosoma brucei gambiense* and *T.b. rhodesiense*[9]. These salivarian parasites are injected into the skin of their host while the tsetse feeds on blood. Previously, the saliva of the tsetse fly *Glossina morsitans morsitans* has been shown to contain a potent inhibitor of mammalian coagulation[10]. While initially reported to function as an "antikinase"[11], it was subsequently shown that the tsetse anticoagulant was most likely an inhibitor of thrombin[10], a serine protease in the mammalian coagulation cascade that cleaves fibrinogen to fibrin, leading to clot formation at sites of vessel damage. In addition to its anticoagulant effect, tsetse saliva also interferes with human platelet aggregation. Some of this activity has been attributed to a low molecular weight fraction of *G.m. morsitans* saliva (MW 11,000–13,000 Da), which acts as a potent inhibitor of thrombin induced platelet aggregation[12].

Tsetse are generally considered one of the single greatest factors affecting the course of economic and social development in Africa. For centuries, tsetse flies have had a great impact on human health, both as efficient vectors of trypanosomes that cause extreme human suffering in African sleeping sickness, and as vectors of trypanosomes that kill non-native animals, preventing the development of animal domestication. More than 30 species of wild animals native to Africa harbor trypanosomes that are pathogenic when transmitted to domestic animals. The disease associated with any of these infections is called nagana. Nagana continues to have a major impact in preventing the development of commercial domestic animal production over about one-third of the African continent. The scarcity of domestic animals results in a severe lack of animal protein for use as human food, a lack of draught animals for use in crop production, and the absence of manure suitable for use as fertilizer. At present, about 40 million cattle and millions of sheep, goats, horses, mules, pigs, and camels are risk of infection in Africa. Unlike African sleeping sickness, in which human disease does not occur over the entire distribution of tsetse vectors, in nagana, domestic animal disease whereever tsetse are found, in additon to other areas where infection can be maintained by mechanical transmission by biting flies other than tsetse.

It would be desirable to provide a new anticoagulant having advantageous properties, and to control the significant morbidity and mortality caused by African sleeping sickness and nagana.

SUMMARY OF THE INVENTION

It is an object of the invention to provide a new anticoagulant useful for medical and veterinary purposes.

It is another object of the invention to provide a potent and specific thrombin inhibitor isolated and purified from tsetse flies.

It is a further and more specific object of the invention to provide a thrombin inhibitor that can be used as an antithrombotic agent and a therapeutic agent for the treatment of numerous vascular disorders such as restenosis following percuntaeous angioplasty, and as a vaccine for trypanosomiasis for human beings and animals.

These and other objects are accomplished by the present invention which provides a soluble protein anticoagulant isolated and purified from *Glossina morsitans morsitans*. This molecule, which is referred to herein as Tsetse Thrombin Inhibitor (herein referred to as TTI), is a novel anticoagulant that appears to represent a new class of serine protease inhibitor. It is a low molecular weight polypeptide, exhibiting a molecular weight of about 3530 Daltons (as determined by laser desorption mass spectrometry, LDMS), that is a potent inhibitor of thrombin.

The polypeptide of the invention, or fragments or variants thereof, are useful as a vaccine or as an active ingredient in variety of pharmaceutical compositions for inhibiting blood coagulation, platelet aggregation, restenosis, metastasis, and combinations thereof.

BRIEF DESCRIPTION OF THE FIGURES

FIG. 4 shows the results of experiments isolating and characterizing the tsetse thrombin inhibitor gene, and illustrates the nucleic acid and polypeptide sequences set out in SEQ ID NOs 1 and 2. A cDNA library was constructed from polyA+ RNA prepared from 1000 pairs of tsetse (*Glossina morsitans morsitans*) salivary glands, and TTI-positive clones were selected which hybridized to degenerate oligonucleotides synthesized according to the N-terminal acmino acid sequence information obtained from purified TTI protein.

DETAILED DESCRIPTION OF THE INVENTION

This invention is based upon the finding that a potent and specific inhibitor of the human coagulation protease thrombin could be obtained as an isolated and purified polypeptide from salivary gland extracts of tsetse flies.

Like other hematophagous arthropods, tsetse flies rely on the production of anticoagulants and antiplatelet agents to facilitate feeding. The adult tsetse fly uses its serrated proboscis to probe the epidermis of its mammalian host, lacerating capillaries and ingesting blood that pools at the site of vessel damage. While tsetse saliva has previously been shown to contain substances that interfere with blood coagulation[10,11] and platelet aggregation[12], little is known about the nature of the antihemostatic molecules responsible for these activities. This invention provides the isolation and characterization of Tsetse Thrombin Inhibitor (TTI), a potent anticoagulant molecule from the saliva of G.m. morsitans.

Figure 3:
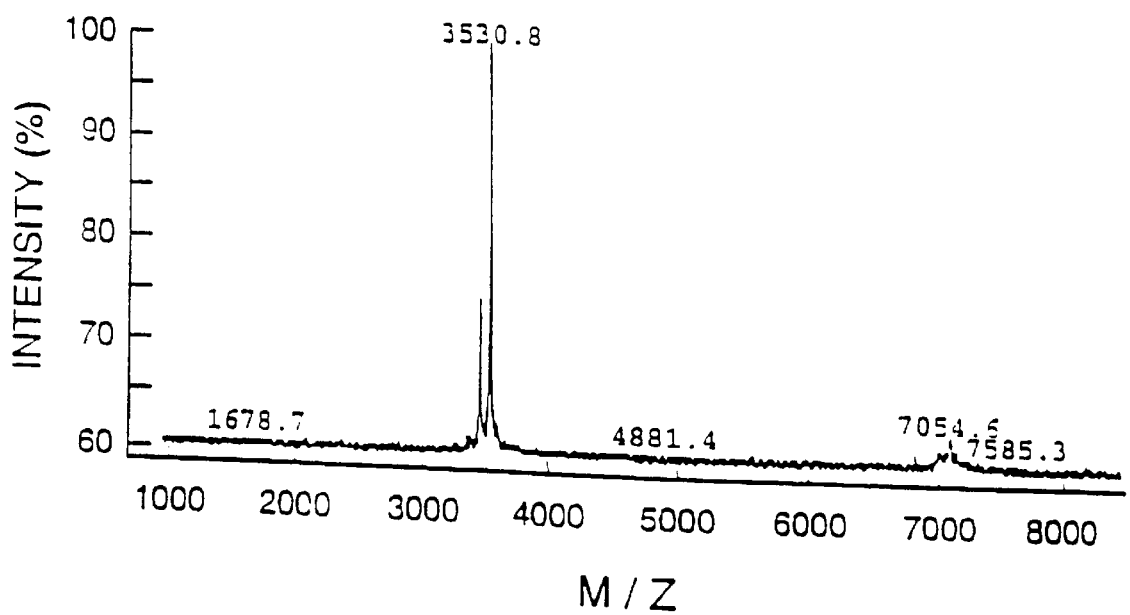
FIG. 3 plots laser desorption mass spectrometry data. The molecular weight of TTI was estimated using LDMS in a matrix of alpha-cyano-4-cinnamic acid. The major peak at 3530.8 represents the single ion, while the smaller peak at 7054.6 likely represents the double ion species.

As described in the Examples section below, TTI was purified from salivary glands using a combination of size exclusion and rpHPLC chromatographies, respectively. The purified protein, which eluted as a single peak on a $C_{18}$ rpHPLC column, was found to have a molecular weight of 3530 Da by LDMS (FIG. 3). Interestingly, this is smaller than the molecular weight estimated by gel filtration (7000–8000 Da), and suggests that TTI may migrate as a dimer under non-reducing conditions. Repeated attempts to visualize the purified protein by SDS-PAGE were unsuccessful, despite using a protocol designed for electrophoresis of low molecular weight proteins[16] with Coomassie and silver staining. However, when gel filtration was repeated, purified TTI still migrated with an apparent molecular weight of about 7000–8000 Da, suggesting that proteolytic breakdown during the purification is not responsible for the difference in estimated molecular weight between gel filtration and LDMS.

The first 20 amino acids of TTI reveal no significant homology to any previously identified serine protease inhibitors, or naturally occurring anticoagulant molecules. While not wishing to be bound to any theory, this suggests that TTI may represent a unique class of protease inhibitor. Sequence information is set out in FIG. 4, more fully described below.

It has previously been reported that fractions of G. morsitans saliva contain at least two distinct inhibitors of platelet aggregation[12]. A higher molecular weight fraction (>30,000 Da) inhibits aggregation induced by ADP, collagen, and adrenalin, possibly due to an ADP hydrolyzing activity present in SGE. A lower molecular weight fraction (11,000–13,000 Da) that inhibits thrombin induced aggregation has also been identified. The data reported in the Examples section hereinafter suggest that TTI, which is a specific inhibitor of thrombin-induced platelet aggregation, may be responsible for this low molecular weight antiplatelet activity previously described by Mant and Parker[12].

G.m. morsitans, an important vector of African trypanosomiasis, has evolved a unique and potent inhibitor of thrombin, which, while not wishing to be bound to any theory, presumably facilitates bloodfeeding by interfering with both coagulation and platelet aggregation within the epidermis of its vertebrate hosts.

This invention thus provides compositions useful in a number of applications, including, but not limited to, vaccines and pharmaceutical compositions more fully discussed below. The invention encompasses the purified polypeptide shown in SEQ ID NO: 2, or fragments or variants thereof, including variants exhibiting at least about 80%, preferably at least about 90%, of the anticoagulant activity and/or platelet aggregation activity of the mature TTI protein. Some embodiments employ a polypeptide corresponding to residues 19 to 50 of SEQ ID NO 2, or fragments or variants thereof. The invention further encompasses synthetic TTI anticoagulants exhibiting activity and structure similar to the isolated and purified polypeptides. Since the polypeptide is small, it can be prepared from its constituent amino acids by sequential formation of peptide bonds using any chemical means. Alternately, the amino acid sequence can be used to prepare cloned complementary DNA sequences defining the anticoagulant of this invention, which can then be used to transform or transfect a host cell for protein expression using standard means. Also encompassed by this invention are DNA sequences homologous or closely related to complementary DNA described herein, namely DNA sequences which hybridize, particularly under stringent conditions, to cDNA encoding thrombin inhibitor of the invention, and RNA corresponding thereto. Many preferred homologue embodiments exhibit an homology of at least about 75%, preferably 85% or greater, to the naturally occurring polypeptide. In addition to the anticoagulant-encoding sequences, DNA encompassed by this invention may contain additional sequences, depending upon vector construction sequences, that facilitate expression of the gene.

Because of the degeneracy of the genetic code, a variety of codon change combinations can be selected to form DNA that encodes the anticoagulant polypeptides of this invention, so that any nucleotide deletion(s), addition(s), or point mutation(s) that result in a DNA encoding the protein are encompassed by this invention. Since certain codons are more efficient for polypeptide expression in certain types of organisms, the selection of gene alterations to yield DNA material that codes for the protein of this invention are preferably those that yield the most efficient expression in the type of organism which is to serve as the host of the recombinant vector. Altered codon selection may also depend upon vector construction considerations.

DNA starting material which is employed to form DNA coding for the anticoagulant of the invention may be natural, recombinant or synthetic. Thus, DNA starting material isolated from tissue or tissue culture, constructed from oligonucleotides using conventional methods, obtained commercially, or prepared by isolating RNA coding for anticoagulant protein, and using this RNA to synthesize single-stranded cDNA which is used as a template to synthesize the corresponding double stranded DNA can be employed to prepare DNA encoding the anticoagulant of this invention.

DNA encoding the protein of this invention, or RNA corresponding thereto, are then inserted into a vector. Host organisms useful in the invention are bacterial (e.g., E. coli or B. subtilis), yeast (e.g., S. cervisiae), insect (e.g., Baculovirus), or mammalian (e.g., mouse fibroblast). This invention thus also provides novel, biologically functional viral and circular plasmid RNA and DNA vectors incorporating RNA and DNA sequences describing the tsetse anticoagulant generated by standard means. Culture of host organisms stably transformed or transfected with such vectors under conditions facilitative of large scale expression of the exogenous, vector-borne DNA or RNA sequences and isolation of the desired polypeptides from the growth medium, cellular lysates, or cellular membrane fractions yields the desired products.

Isolation and purification of expressed polypeptides provided by the invention are typically by conventional means including, for example, preparative chromatographic separations such as that illustrated in the Examples, and immunological separations, including monoclonal and/or polyclonal antibody preparations.

The tsetse thrombin inhibitor of this invention exhibits a number of desirable characteristics. Unlike other anticoagulants derived from blood feeding parasites, it is small enough that it can be synthesized, and its sequences suggests that the mature protein has little tertiary structure. In addition, TTI is comparable in potency to other thrombin inhibitors, including hirudin, although it is significantly smaller. It thus has uses as a therapeutic anticoagulant for many disease conditions such as heart disease, stroke, pulmonary embolism, and deep vein thrombosis, and as an anti-restenosis, antimetatastic, and anti-inflammatory agent. In the methods encompassed by the invention, for example, a patient is treated by administering to a patient a composition comprising an effective amount of a polypeptide shown in SEQ ID NO: 2, particularly a polypeptide corresponding to residues 19 to 50 of SEQ ID NO 2, or fragments or residues thereof, to inhibit blood coagulation, platelet aggregation, metastasis, restenosis, or combinations of thereof.

Percutaneous transluminal coronary angioplasty (PTCA) has gained wide-spread acceptance in the treatment of coronary artery disease, representing a suitable alternative in many instances to bypass graft surgery. The major drawback to PTCA is the development of acute reocclusion and restenosis, which occur in up to half of those undergoing the procedure. The pathogenesis of restenosis, which develops soon after balloon dilatation of the affected artery, has recently become an area of intense scientific investigation. It is likely that the initial vascular damage caused by the procedure itself initiates a cascade of endothelial cell responses that ultimately leads to intimal smooth muscle cell proliferation and reocclusion. It has been shown in animal models that angioplasty results in denudation of the endothelial surface, with platelet deposition, mural thrombus formation, and medial smooth muscle cell proliferation identified at 24 hours[20]. Accelerated smooth muscle cell growth proceeds over the next 14 days, with restenosis occurring as soon as 4 weeks after the initial procedure. Autopsy data on individual in the early post-angioplasty period appear to corroborate the findings from animal studies regarding the time course of reocclusion and restenosis[21]. While platelet deposition and mural thrombus formation probably cause acute reocclusion, the pathogenesis of restenosis is less well understood.

Work on the mechanisms underlying restenosis has identified an intriguing relationship between specific coagulation factors and the proliferation of smooth muscle cells associated with intimal hyperplasia. It appears that in addition to their roles as initiators of the hemostatic response, certain coagulation proteases are potent mitogens for a variety of cell types, including smooth muscle cells. Gasic, et al., have shown that factor X, thrombin, and protein S all stimulate growth of cultured rat aorta cells[22]. In addition, thrombin stimulates proliferation of fibroblasts, macrophages, and smooth muscle cells, in addition to its role as a potent procoagulant. Enzymatically active thrombin has been identified within the intima of damaged endothelium, where it is functionally protected from circulating inhibitors like antithrombin III and heparin[23]. This pool of thrombin may contribute to the intimal proliferation that characterizes restenosis following vessel damage. In support of this theory is a growing body of evidence that suggests that activation of the thrombin receptor is associated with a variety of intracellular signalling events[24].

The role of the coagulation cascade in the growth and spread of malignant cells has long been the subject of scientific inquiry. For example, it has been shown that certain circulating tumor cells often become coated with fibrin, the basic substance of which mammalian blood clots are made. Moreover, fibrin deposition has also been documented within solid tumor masses, and patients with cancer often experience compilations related to a "hypercoagulable state," perhaps caused by increased levels of clotting factors circulating within the bloodstream. While this association between clotting and cancer has been documented previously, little is known about the potential role of therapy aimed at inhibiting the thrombotic activity of cancer cells as a means of limiting tumor growth and metastasis.

Over the past ten years, the development of contemporary molecular techniques has allowed for the identification of specific receptors for individual molecules involved in the regulation of human blood clotting on the surface of certain types of tumor cells. Most of these coagulation factors are serine proteases that initiate or propagate the clotting cascade, including factor VIIa, factor Xa, and thrombin. It has been hypothesized that single tumor cells, when they are released into the bloodstream, utilize the coagulation cascade to lodge themselves in tissues far from the site of the original tumor. Once cemented within the fibrin matrix of a blood clot, the tumor cell can begin to multiply in its new site. In fact, for certain types of cancer cells, clotting mechanisms are thought to play a major role in their ability to metastasize.

Some of the human malignancies whose cells possess receptors for one or more of these clotting factors include ovarian cancer, renal cell carcinoma, melanoma, breast cancer and small cell cancer of the lung. Taken together, these tumors account for a significant number of deaths among adults in the United States. Moreover, they each carry a relatively poor prognosis, even when the most aggressive contemporary chemotherapy regimens are employed. Evidence from large clinical trials suggests that long term anticoagulant therapy may actually reduce cancer related mortality for certain malignancies. Unfortunately, currently available anticoagulants, e.g., heparin and warfarin, are inherently difficult to administer safely, often leading to dangerous bleeding complications. It is an advantage of the invention that it provides a way to act on the clotting factor specific to the tumor itself.

Limited work in animal models of angioplasty and vessel damage has revealed that specific inhibition of thrombin or factor Xa represents a viable approach to limiting restenosis. Sarembock, et al., have shown that recombinant hirudin, the leech derived thrombin inhibitor, was more effective at maintaining vascular patency 28 days following antioplasty than standard heparin[25]. Rabbits that received intravenous hirudin for two hours post procedure had significantly less cross sectional narrowing of the affected vessel as shown by histologic sectioning. More recent data suggest that inhibition of factor Xa at the time of antioplasty may be equally effective. Ragosta, et al., found in a similar model that both recombinant antistasin (from the leech, *Haementaria officinalis*) and tick anticoagulant peptide (from *Ornithodoros moubata*), two potent and specific inhibitors of factor Xa, were superior to heparin in reducing restenosis following angioplasty in rabbits[26]. While the mechanism of anti-restenosis action of these naturally occurring anticoagulants remains to be elucidated, it is likely that their effect is due to both anticoagulant and antiproliferative effects.

Thus the invention provides anticoagulant products for veterinary and medical purposes such as deep vein thrombosis, as well as antirestenotic compositions and compositions useful in the treatment of certain cancers. The thrombin inhibitor of the invention has further utility in the treatment of unstable angina and myocardial infarction. Administration of tsetse thrombin inhibitor of the invention can be local or systemic. Systemic administration is preferred in some embodiments. Administration can be via any method known in the art such as, for example, oral administration of losenges, tablets, capsules, granules, or other edible compositions; subcutaneous, intravenous, intramuscular, or intradermal administration, e.g., by sterile injections; parenteral administration of fluids and the like. Typical administrations involve the use of the inhibitor dispersed or solubilized in a pharmaceutically acceptable carrier.

Local administration is preferred in other embodiments. In these embodiments, the inhibitor, again preferably in association with a pharmaceutically acceptable carrier in which the inhibitor is dispersed or solubilized, is applied in effective amounts directly to an organ. Combinations of therapies may also be employed.

The amount of inhibitor necessary to bring about the therapeutic treatment is not fixed per se, and necessarily is dependent on the concentration of ingredients in the composition administered in conjunction with a pharmaceutical carrier, adjunct compounds in the composition administered that enhance the inhibitory effect where present, and the age, weight, and clinical condition of the patient to be treated. Preferred compositions deliver the thrombin inhibitor in effective amounts without producing unacceptable toxicity to the patient. Pharmaceutical compositions or formulations of the invention may also include other carriers, adjuvants, stabilizers, preservatives, dispersing agents, and other agents conventional in the art having regard to the type of formulation in question.

In addition, enhancement of an immune response aimed at the tsetse thrombin inhibitor of the invention provides a vaccine for reducing the burden of African trypanosomiasis in populations at risk, and for nagana in animals, particularly domestic animals. As summarized above, both sleeping sickness and nagana are devastating diseases. As an antigen, the protein of this invention thus has utility for vaccination for trypanosomiasis and nagana. This typically involves immunizing a mammal (animal or human being) by inoculating the mammal with an effective amount of a product prepared by mixing the protein with a suitable carrier such as isotonic saline.

EXAMPLES

The following examples are presented to further illustrate and explain the present invention and should not be taken as limiting in any regard.

Example 1

Isolation and Characterization of TTI

MATERIALS AND METHODS

Materials. S-2765 (factor Xa) and S-2238 (thrombin) substrates were purchased from Kabi Pharmacia Hepar (Franklin, Ohio). The chromogenic substrates were reconstituted in deionized water prior to use.

Salivary gland extract (SGE). Salivary glands were dissected from live *G.m. morsitans* adult tsetse flies and placed in cold 50 mM Tris-HCl, pH 7.5. SGE was prepared by vortexing the glands for 30 s in a 1.5 ml eppendorf tube followed by centrifugation at 14,000 g for 30 min at room temperature. The supernatant was collected and the pellet resuspended in Tris buffer and again vortexed. After centrifugation, the supernatants were pooled and concentrated to approximately 0.5 ml in a Centricon 3 concentrator (Amicon). The protein concentration of SGE was determined using a modified method of Bradford[14].

Size Exclusion Chromatography. SGE from approximately 200 glands in a volume of 0.2 ml was applied to a Pharmacia Superdex 75 HR 10/30 gel filtration column (1×30 cm) equilibrated with 50 mM Tris-HCl, pH 7.5, 200 mM NaCl, using a Fast Pressure Liquid Chromatography (FPLC) system (Pharmacia) at 25° C. with a flow rate of 0.25 ml/min. Individual column fractions (0.5 ml) were tested for protein concentration and thrombin inhibition. The anti-thrombin activity from two separate column runs was pooled and concentrated to approximately 0.5 ml.

Reverse phase HPLC. Following gel filtration, the pooled and concentrated thrombin inhibitory activity was subjected to reverse phase High Performance Liquid Chromatography (rpHPLC) using a Vydac (Hesperia, Calif.) $C_{18}$ column (0.46×25 cm, 5μ pore size) equilibrated with 2% acetonitrile in 0.1% trifluoroacetic acid (TFA). Protein was eluted from the column by a gradient of acetonitrile (2–60% over 90 min) in 0.1% TFA at a constant flow rate of 0.25 ml/min. Individual peaks of protein as detected by absorbance at 210 nm were collected and assayed for thrombin inhibition.

Amino Acid Analysis and $NH_2$-terminal Sequencing. Amino acid analysis was obtained on a Beckman 6300 Amino Acid Analyzer after hydrolyzing the sample for 20 hours in 6N HCl, 0.2% phenol. Following Edman degradation, approximately 500 picomoles of TTI was injected into an Applied Biosystems Model 470A gas phase sequencer equipped with a Model 120A PTH analyzer.

Laser Desorption Mass Spectrometry. TTI's molecular weight was determined by laser desorption mass spectrometry (LDMS) using a VG/Fisons TofSpec in the positive ion mode with a nitrogen laser (337 nm) at an acceleration voltage of 25,000. Following rpHPLC, 1 μl (approximately 2 picomoles) of purified TTI was added to 1 μl of a 10 mg/ml alpha-cyano-4-cinnamic acid matrix solution in 0.1% TFA/40% acetonitrile. The expected mass accuracy for peptides below the 1.0 picomole level using external calibration was +/−0.25%.

Thrombin Assays. A single stage chromogenic assay of thrombin inhibition was used to monitor SGE activity. 100 μl of thrombin, diluted to a concentration of 1 nM in 10 mM HEPES, pH 7.5 containing 0.1% bovine serum albumin and 150 mM NaCl (HBSA), was incubated with 50 82 1 of SGE, column fractions (diluted 1:1000 in HBSA), or purified TTI for 15 min at 25° C. in a 96 well microtiter plate. Following the addition of 50 S-2238, the initial rate (mOD/min) of substrate hydrolysis over 5 min was measured at 405 nm using a Vmax kinetic microplate reader (Molecular Devices, Palo Alto, Calif.). Results were expressed as percent inhibition of thrombin activity using the following formula:

Percent inhibition=1—(inhibited rate/uninhibited rate)×100

Platelet Aggregation Assay. Blood from a healthy human volunteer was collected by venipuncture, anticoagulated with 1/10 volume of 0.08 M trisodium citrate, and centrifuged at 150 g for 10 min. The platelet rich plasma (PRP) was withdrawn and acidified to pH 6.4 using 0.15 M citric acid[15]. The PRP was then centrifuged at 370 g for 20 min and the supernatant discarded. The platelet pellet was resuspended in Tyrodes solution (pH 7.4) with 3.13% wt/vol trisodium citrate and counted in a Coulter counter (Coulter Electronics, Hialeah, Fla.). The concentration of platelets was adjusted to $3 \times 10^4/\mu l$ prior to use.

To determine the effect of TTI on thrombin induced aggregation, 200 μl of washed platelets were warmed to 37° C. in a Born multi-channel aggregometer in the presence of increasing concentrations of purified TTI. Aggregation was then recorded following the addition of 20 μl of thrombin (Boehringer-Mannheim, Indianapolis, Ind.) at a final concentration of 0.2 NIH U/ml. The aggregometer was calibrated to 100% light transmission, ie 0% aggregation, using Tyrodes solution.

Construction of a cDNA Library. Total RNA was purified from 1000 pairs of salivary glands of Glossina morsitans morsitans flies using the protocol from Chirgwin, et al.[18] Poly(A)+ RNA was prepared following the protocol of Maniatis, et al.,[19]. Uni-Zap XR Vector Kit from Stratagene (La Jolla, Calif.) was used to generate a unidirectional cDNA library. Briefly stated, first-strand synthesis is primed with the oligo-dT primer/linker that contains an XhoI site and transcribed using Maloney reverse transcriptase and 5-methyl-dCTP. RNAseH is used for the second-strand synthesis in association with DNA polymerase I and EcoRI adaptors are ligated to the blunted ends. The cDNA molecules are cleaved with EcoRI and XhoI and are ligated to the Uni-ZAP XR vector arms and packaged using the Gigapack III Gold packaging extracts (Stratagene #237612) and plated on the E. coli cell line SURE. The library was plated and plaques were transferred to nitrocellolose filters.

Selection of TTI-Containing Clones. Two oligonucleotide probes were synthesized based on the N-terminal amino acid sequence information obtained from the purified TTI protein. Probe I was GGIIGARCCIGGIGCTCCIATIGAYTA (SEQ ID NO: 3), and probe 2, ATIGAYTAYGAYGAR-TAYGGIGGIGA (SEQ ID NO: 4). The oligonucleotides were end-labelled with γ-P$^{32}$ATP and were used as hybridization probes to screen the library. (Hybridization conditions were 50% formamide/5×Denharts/5×SSC/0.5% SDS at 42° C. and the filters were washed to a final stringency of 5×SCC at 42° C.) Positive plaques were picked, rescreened and the phagemids containing the insert was excised using the helper phage f1 according to Stratagene instructions.

RESULTS

Figure 1:
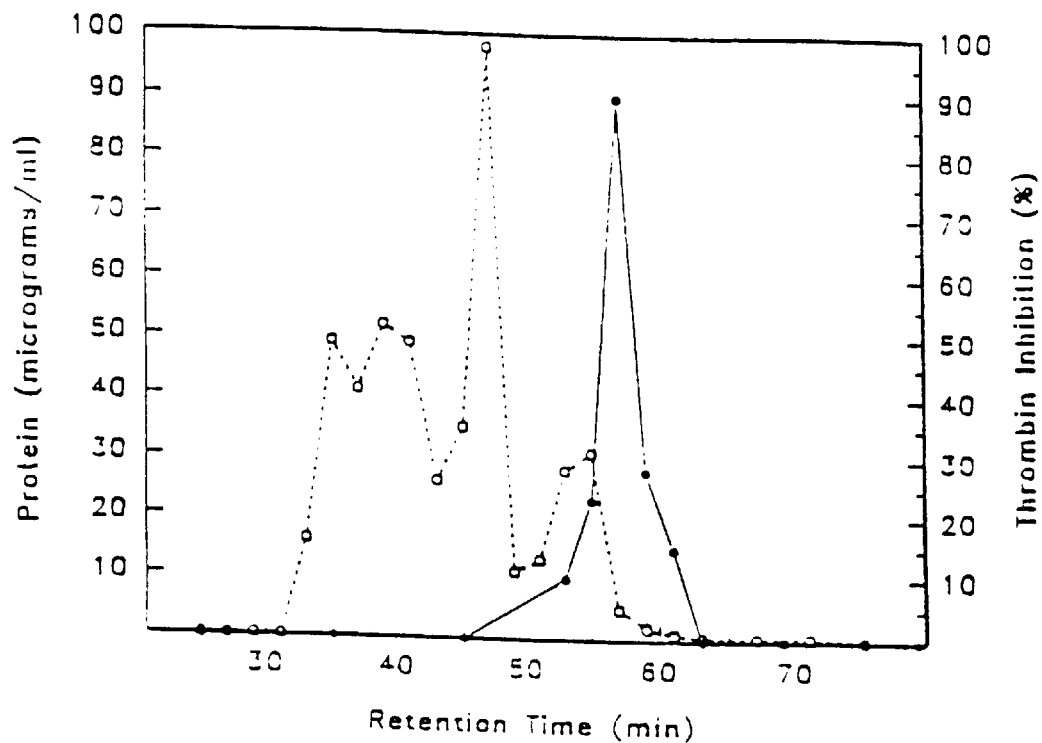
FIG. 1 is a line graph showing size exclusion chromatography data. SGE from 200 adult tsetse flies was applied to a Superdex HR 10/30 size exclusion column (Pharmacia) at a flow rate of 0.25 ml/min. Column fractions (0.5 ml) were assayed for protein concentration (open circles) and thrombin inhibition (closed circles) as described in the Methods section of the Examples. A single peak of anti-thrombin activity was identified, with an estimated molecular weight of 7,000–8,000 Da based on extrapolation from a standard curve using proteins of known molecular size.
Figure 2:
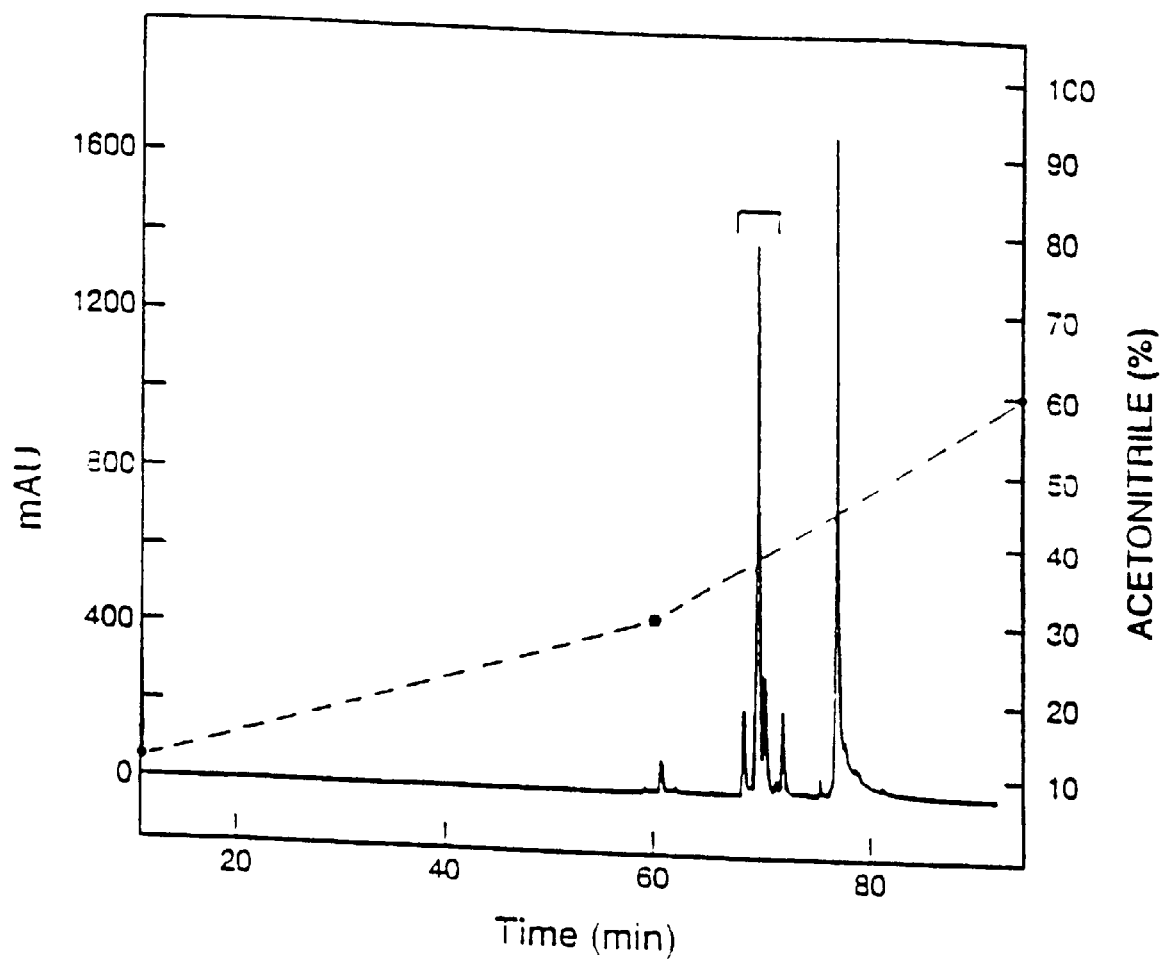
FIG. 2 is a line graph plotting rpHPLC data regarding TTI. Following size exclusion, the pooled anti-thrombin activity was subjected to rpHPLC using a Vydac $C_{18}$ column equilibrated with 2% acetonitrile in 0.1% TFA. TTI eluted as a single peak of protein (see bracket) under a gradient of 2–60% acetonitrile (dashed line).

Purification of the Anti-Thrombin Activity. The tsetse thrombin inhibitor (TTI) was purified from adult G.m. morsitans salivary gland extract (SGE) using a combination of size exclusion (FIG. 1) and rpHPLC (FIG. 2) chromatographies, respectively. Approximately 14 μg of purified inhibitor was recovered from 400 adult salivary glands containing approximately 1.5 μg total protein/gland. The final yield of TTI from the purification was approximately 24%.

Following rpHPLC, the purified inhibitor was subjected to amino acid analysis (Table 1) and NH$_2$-terminal sequencing (Table 2). Twenty amino acids were unambiguously determined, and searches of three peptide sequence databases (genpept, pdb, and swissprot) through the National Center for Biotechnology Information revealed no significant homology to any previously reported protein sequences.

TABLE 1

Amino acid composition of TTI. 3.597 μg of protein were analyzed. Cysteine and tryptophan residues were not determined.

| Amino acid | Residues per $M_r$ = 3530 |
|---|---|
| Asx | 3.3 |
| Thr | 1.0 |
| Ser | 1.6 |
| Glx | 5.4 |
| Pro | 4.2 |
| Gly | 6.4 |
| Ala | 1.2 |
| Ile | 4.1 |
| Leu | 2.2 |
| Tyr | 2.0 |
| His | 1.1 |
| Lys | 0.1 |
| Arg | 1.0 |
| Total residues: 34 | |

TABLE 2

NH$_2$-terminal sequence of TTI. Initial sequencing yield based on residue #2 (Glu) is approximately 20%.

| Residue | Amino Acid | Yield (pM) |
|---|---|---|
| 1 | Gly | 212.1 |
| 2 | Glu | 97.0 |
| 3 | Pro | 134.8 |
| 4 | Gly | 152.5 |
| 5 | Ala | 211.9 |
| 6 | Pro | 119.0 |
| 7 | Ile | 156.2 |
| 8 | Asp | 7.3 |
| 9 | Tyr | 94.8 |
| 10 | Asp | 3.4 |
| 11 | Glu | 58.5 |
| 12 | Tyr | 64.2 |
| 13 | Gly | 51.6 |
| 14 | Asp | 1.3 |
| 15 | Ser | 21.5 |
| 16 | Ser | 25.6 |
| 17 | Glu | 6.0 |
| 18 | Glu | 10.7 |
| 19 | Ile | 8.8 |
| 20 | Gly | 6.7 |

The molecular weight of TTI as determined by LDMS is 3530 Da (FIG. 3), which is approximately half that estimated by size exclusion chromatography. Repeat gel filtration of purified TTI confirmed that the purified protein migrates at the same estimated molecular weight as the anti-thrombin activity contained within SGE (7000–8000 Da).

Analysis of Assay Results. Assays of the inhibitory activity of TTI revealed that this molecule is a potent, tight-binding inhibitor of thrombin.

The anti-thrombotic activity of TTI was also evaluated in standard platelet aggregation assays. Four concentrations of TTI (1=0 nM, 2=0.001 nM, 3=0.5 nM, 4=1.0 nM) were employed. The data showed dose dependent inhibition of platelet aggregation in response to thrombin. Thus, TTI is a potent inhibitor of thrombin-induced platelet aggregation. This anti-platelet effect was specific, since purified TTI had no effect on either ADP or collagen induced aggregation.

DNA Sequence of the TTI-Encoding cDNA-Insert. The DNA sequence of the insert from one positive phagemid clone was determined using the dideoxy chain-termination approach. The insert had 269 nt. It had an open reading frame of 56 nt at the 5'-end before the mature coding sequence of the TTI protein is encountered, the next 32 amino acids correspond to the mature TTI sequence before the first stop codon. There are 99 nt of 3-untranslated sequence before 19 poly(A) residues as shown in FIG. 4. The underlined second reading frame corresponds to the correct reading frame.

Example 2

Expression and Purification of Recombinant TTI

Oligonucleotide primers with engineered restriction sites and corresponding to the sequence of the mature TTI protein (corresponding to residues 19 to 50 of SEQ ID NO: 2: see also the underlined polypeptide portion of FIG. 4) were synthesized and used to amplify the TTI cDNA by PCR. The PCR product was digested with the restriction enzymes NcOI and XhOI, gel purified and cloned into the prokaryotic expression vector pET 32a (Novagen).

The pET 32a plasmid DNA containing the ligated TTI CDNA was used to transform *E. coli* DH5α cells, and individual colonies were screened for the presence of the insert by both PCR with TTI-specific primers and restriction enzyme digest of plasmid DNA. Miniprep plasmid DNA from a positive colony was subsequently used to transform *E. coli* BL21 cells, which were again plated and screened by PCR for presence of the TTI cDNA.

A 3 ml overnight culture of bacteria was grown in LB media with ampicillin from an isolated BL21 colony shown to possess the plasmid containing the TTI insert. A 500μ aliquot of this culture was used to inoculated 500 ml of media and was incubated at 37° C. with vigorous shaking (250 rpm) until the $OD_{600}$ reached 1.0. At this time, expression was induced by the addition of isopropyl-β-D-thiogalactosylpyranoside (IPTG) to a final concentration of 1 mM. The cells were pelleted after 3 hours of continued incubation at 37° C., and resuspended in 10 ml of 1× binding buffer (5 mM imidazole, 500 mM NaCl, 20 mM Tris-HCl, pH 7.9). Following sonication for 3 minutes on ice, the lysed cell extract was centrifuged at 20,000×g for 30 minutes at 4° C.

The soluble lysate was applied to a 6 ml His-Bind resin column (Novagen) charged with 50 mM $NiSO_4$ and then equilibrated with 1× binding buffer. After washing with 5 column volumes of 1× wash buffer (60 mM imidazole, 500 mM NaCl, 20 mM Tris-HCl, pH 7.9), the bound protein was eluted with 500 mM imidazole in 20 mM Tris-HCl, pH 7.9, 500 mM NaCl. The partially purified recombinant TTI was then subjected to reverse phase HPLC (rpHPLC) using a Vydac™ (Hesparia, Calif.) $C_{18}$ column equilibrated with 10% acetonitrile in 0.1% trifluoroacetic acid (TFA) at a flow rate of 0.5 ml/min. The bound protein was eluted with a linear gradient of 10–40% acetonitrile in 0.1% TFA. Individual peaks of protein as detected by $OD_{210}$ were collected and assayed for inhibition of thrombin. SDS-PAGE according to the method of Schagger and von Jagow (*Anal. Biochem.* 1987, 166:368–379) was used to monitor the purification of rAcAP. The purified recombinant TTI (rTTI) was shown to have an estimated molecular weight of approximately 19–21 kDa by SDS-PAGE.

The protein concentration of the purified RTTI was measured using the BCA assay kit (Pierce). The purified rTTI was found to inhibit purified thrombin using the previously described single stage chromogenic assay.

Example 3

Characterization of TTI Sequences and Regulation of Expression

Tsetse DNA genomic library is constructed in a cosmid vector. TTI encoding genomic sequences are isolated from the library using the cDNA mature-protein encoding sequences as hybridization probes. The TTI-encoding sequences are determined by DNA sequencing analysis. The 5'-end upstream sequences are analyzed. These sequences correspond to the complete TTI-encoding region as well as the transcription regulatory regions. These promoter sequences are used to express other foreign genes. Since TTI is a secretory protein found in saliva, fusion proteins expressed under regulation of the TTI promoter and secretary signal sequences can be secreted out into the saliva.

The tissue-specific expression of the TTI protein is determined by Northern blot analysis of MRNA. The polyadenylated mRNA is s elected from specific tissues (salivary gland, midgut, muscle, reproductive tissue) and analyzed using the TTI cDNA gene clone as a hybridization probe. The developmental regulation of expression of TTI is studied by analyzing mRNA from different larval and pupal stages as well as the adult stage of the fly.

The above description is intended to enable a person skilled in the art to practice the invention. It is not intended to detail all of the possible modifications and variations which will become apparent to the skilled worker upon reading the description. It is intended, however, that all such modifications and variations be included within the scope of the invention. Elements and steps in the practice of the invention may be in any arrangement or sequence which is effective to meet the objectives intended for the invention, unless the context specifically indicates the contrary.

REFERENCES

1. Waxman, L, Smith, D E, Arcuri, K E, Viasuk, G P, 1990. Tick Anticoagulant peptide (TAP) is a novel inhibitor of blood coagulation factor Xa. *Science* 248:593–596.
2. Ribeiro, J M C, Makoul, G T, Levine, J, Robinson, D R, Spielman, A, 1985. Antihemostatic, antiinflammatory, and immunosuppressive properties of the saliva of a tick, *Ixodes Dammini*. *J Exp Med* 161:332–344.
3. Lerner, E A, Ribeiro, J M C, Nelson, R J, Lerner, M R, 1991. Isolation of maxadilan, a potent vasodilatory peptide from the salivary glands of the sand fly *Lutzomyia longipalpis*. *J Biol Chem* 266:11234–11236.
4. Friedrich, T, Kroger, B, Bialojan, S, Lemaire, H G, Hoffken, H W, Reuschenbach, P, Otte, M, Dodt, J. 1993. A Kazal-type inhibitor with thrombin specificity from *Rhodnius prolixus*. *J Biol Chem* 268:16216–16222.
5. Sarkis, J J F, Guimaraes, J A, Ribeiro, J M C, 1986. Salivary apyrase of *Rhodnius prolixus*: kinetics and purification. *Biochem J* 233:885–891.
6. Jacobs, J W, Cupp, E W, Sardana, M, Friedman, P A, 1990. Isolation and characterization of a coagulation factor Xa inhibitor from black fly salivary glands. *Thromb Haemost* 64:235–238.
7. Champagne, D E, Ribeiro, J M C, 1994. Sialokinin I and II: vasodilatory peptides from the yellow fever mosquito *Aedes aegypti*. *Proc Natl Acad Sci USA* 91:138–142.
8. Ribeiro, J M C, Sarkis, J J F, Rossignol, P A, Spellman, A, 1984. Salivary Apyrase of *Aedes aegypti*: characterization and secretory fate. *Comp Biochem Physiol* 79B:81–86.
9. Lehane, M J, 1991. *Biology of Blood-Sucking Insects* London: HarperCollins, 143.
10. Parker, K R, Mant, M J, 1979. Effects of tsetse (*Glossina morsitans morsitans Westw.*) (Diptera: Glossinidae) salivary gland homogenate on coagulation and fibrinolysis. *Thromb Haemost* 42:743–751.
11. Lester, H M O, Lloyd, L, 1926. Notes on the process of digestion in tsetse flies. *Bull Entomol Res* 19:39–60.

12. Mant, M J, Parker, K R, 1981. Two platelet aggregation inhibitors in tsetse (Glossina) saliva with studies of roles of thrombin and citrate in in vitro platelet aggregation. *Br J Haemat* 48:601–608.
13. Bock, P E, Craig, P A, Olson, S T, Singh, P, 1989. Isolation of human blood factor Xa by soybean trypsin inhibitor-sepharose chromatography and its active site titration with fluorescein mono-p-guanidobenzoate. *Arch Biochem Biophys* 273:375–388.
14. Bradford, M M, 1976. A rapid and sensitive method for the quantitation of microgram quantities of protein utilizing the principle of protein-dye binding. *Anal Biochem* 72:248–254.
15. Lagarde, M, Bryon, P A, Guichardant, M, Dechavanne, M, 1980. A simple and efficient method for platelet isolation from their plasma. *Thromb Res* 17:381–388.
16. Schagger, H, von Jagow, G, 1987. Tricine-sodium dodecyl sulfate-polyacrylamide gel electrophoresis for the separation of proteins in the range from 1 to 100 kDa. *Anal Biochem* 166:368–379.
17. Marki, W E, Wallis, W B, 1990. The anticoagulant and antithrombotic properties of hirudins. *Thromb Haemost* 64:344–348.
18. Chirgwin, J M, Przybyla, A E, MacDonald, R J, and Rutter, W J (1979) Isolation of biologically active ribonucleic acid from sources enriched in ribonuclease. *Biochemistry* 18:5294–5299.
19. Maniatis, T, Fritsch, E F, and Sambrook, J, 1989. *Molecular Cloning. A Laboratory Manual.* Cold Spring Harbor Laboratory, Cold Spring Harbor, N.Y.
20. Ip, J H, Fuster, V, Badimon, L, et al., 1995. Syndromes of accelerated atherosclerosis: role of vascular injury and smooth muscle cell proliferation. *JACC* 15:1667–87.
21. Waller, B F, Gorfinkel, H J, Rogers, F J, et al., 1984. Warly and later morphological changes in major epicardial coronary arteries after percutaneous transluminal coronary angioplasty. *Am J Cardiol* 53 (suppl C):42C-7C.
22. Gasic, G P, Arenas, C P, Gasic, T B, Gasic, G J, 1992. Coagulation factors X,Sa, and protein S as potent mitogens of cultured aortic smooth muscle cells. *Proc Natl Acad Sci USA* 89:2317–2320.
23. Bar-Shavit, R, Benezra, M, Eldor, A, et al., 1990. Thrombin immobilized to extracellular matrix is a potent mitogen for vascular smooth muscle cells: nonenzymatic mode of action. *Cell Reg* 1:453–463.
24. Fischer, E G, Ruf, W, Mueller, B M, 1995. Tissue factor-initiated thrombin generation activates the signaling thrombin receptor on malignant melanoma cells. *Cancer Res* 55:1629.
25. Sarembock, U, Gertz, S D, Gimple, L W, et al., 1991. Effectiveness of recombinant desuiphatohirudin in reducing restenosis after balloon angioplasty of atherosclerotic femoral arteries in rabbits. *Circulation* 84:232–243.
26. Ragosta, M, Gimple, L W, Gertz, S D, et al., 1994. Specific factor Xa inhibition reduces restenosis after baloon angioplasty of atherosclerotic femoral arteries in rabbits. *Circulation* 89:1262–1271.
27. Cappello, M. Clyne, L P, McPhedran, P, Hotez, P J, 1993. Ancylostoma factor Xa inhibitor: partial purification and its identification as a major hookworm-derived anticoagulant in vitro. *J Infect Dis* 167:1474–7.
28. Capello, M, Viasuk, G P, Bergum, P, Huang, S, Hotez, P J, 1995. *Ancylostoma caninum* anticoagulant peptide: a hookworm derived inhibitor of human coagulant factor Xa. *Proc Nati Acad Sci USA* 92:6152.

All the papers cited herein are hereby incorporated in their entireties by reference.

We claim:

1. A purified polypeptide shown in SEQ ID NO: 2.

2. A polypeptide corresponding to residues 19 to 50 of SEQ ID NO: 2, or a fragment or variant thereof exhibiting at least about 75% sequence homology to the naturally occuring polypeptide, wherein said fragment or variant inhibits thrombin.

3. A polypeptide according to claim 2, wherein the fragment or variant exhibits at least about 85% sequence homology to the naturally occurring polypeptide.

4. A polypeptide corresponding to residues 19 to 50 of SEQ ID NO: 2.

5. A pharmaceutical composition comprising the polypeptide of claim 2.

6. A composition according to claim 5 which exhibits anticoagulant activity.

7. A composition according to claim 5 which inhibits platelet aggregation.

8. A composition for inducing the immune response of a mammal comprising the polypeptide of claim 2.

9. A composition for inducing the immune response of a mammal susceptible to African trypanosomiasis comprising the polypeptide of claim 2.

10. A composition for inducing the immune response of a mammal susceptible to nagana comprising a polypeptide according to claim 2.

11. A method for treating a patient comprising administering a composition comprising an effective amount of the polypeptide according to claim 2 to the patient, to inhibit blood coagulation or platelet aggregation.

12. A composition for inducing the immune response of a mammal comprising the polypeptide of claim 1.

13. A composition for inducing the immune response of a mammal susceptible to African trypanosomiasis comprising the polypeptide of claim 1.

14. A composition for inducing the immune response of a mammal susceptible to nagana comprising the polypeptide of claim 1.

* * * * *

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 268
      (B) TYPE: nucleic acid
      (C) STRANDEDNESS: single
      (D) TOPOLOGY: linear (ii) MOLECULE TYPE:
      (A) DESCRIPTION: cDNA (ix) FEATURE:
      (A) NAME/KEY: tsetse thrombin inhibitor (xi) SEQUENCE DESCRIPTION: SEQ ID NO: 1:

```
CACGAGGTAC TATTTTTCTT GCTCAGCATT ATTTATCTGA TAGTTGCCGC          50

ACCTGGTGAA CCAGGTGCAC CCATAGATTA TGACGAATAC GGGGATAGCA         100

GCGAAGAAGT TGGTGGCACA CCTTTGCATG AGATTCCTGG CATAAGGCTT         150

TAATTTAGTA CCAGAAGAAG AATTGATTAA GATCAGTTCG TCCGAATTTG         200

TAAAGTTCGA AGAAATAAAT GCATAAAAAA GAATAATATT GATGCAACTA         250

AAAAAAAAAA AAAAAAAA                                            268
```

```
(2) INFORMATION FOR SEQ ID NO: 2:

(i) SEQUENCE CHARACTERISTICS:
        (A) LENGTH: 50 amino acids
        (B) TYPE: amino acid
        (C) STRANDEDNESS: single
        (D) TOPOLOGY: linear (ii) MOLECULE TYPE:
        (A) DESCRIPTION: polypeptide (vi) ORIGINAL SOURCE:
        (A) ORGANISM: Glossina morsitans morsitans
        (B) INDIVIDUAL ISOLATE: adult salivary glands (vii) IMMEDIATE SOURCE:
        (A) LIBRARY: construct from native RNA
        (D) CLONE: TTI-positive (ix) FEATURE:
        (A) NAME/KEY: putative TTI cDNA polypeptide
        (D) OTHER INFORMATION:  residues before a stop codon
            at position 51

(xi) SEQUENCE DESCRIPTION: SEQ ID NO:2:

His Glu Val Leu Phe Phe Leu Leu Ser Ile Ile Tyr Leu Ile Val
                5                   10                  15

Ala Ala Pro Gly Glu Pro Gly Ala Pro Ile Asp Tyr Asp Glu Tyr
                20                  25                  30

Gly Asp Ser Ser Glu Glu Val Gly Gly Thr Pro Leu His Glu Ile
                35                  40                  45

Pro Gly Ile Arg Leu
                50

(2) INFORMATION FOR SEQ ID NO: 3:

(i) SEQUENCE CHARACTERISTICS:
        (A) LENGTH:  27 bases
        (B) TYPE: nucleic acid
        (C) STRANDEDNESS: single
        (D) TOPOLOGY: linear (ii) MOLECULE TYPE:  DNA
        (A) DESCRIPTION: primer used in constructs (ix) FEATURE:
        (A) NAME/KEY: primer
        (D) OTHER INFORMATION: N at position 10 is unknown;
            the other Ns represent I (xi) SEQUENCE DESCRIPTION: SEQ ID NO:3:

GGNNGARCCN GGNGCTCCNA TNGAYTA                                           27

(2) INFORMATION FOR SEQ ID NO: 4:

(i) SEQUENCE CHARACTERISTICS:
        (A) LENGTH:  26 bases
        (B) TYPE: nucleic acid
        (C) STRANDEDNESS: single
        (D) TOPOLOGY: linear (ii) MOLECULE TYPE:  DNA
        (A) DESCRIPTION: primer used in constructs (ix) FEATURE:
        (A) NAME/KEY: primer
        (D) OTHER INFORMATION: N represents I (xi) SEQUENCE DESCRIPTION: SEQ ID NO:4:

ATNGAYTAYG AYGARTAYGG NGGNGA                                            26
```

```
(2) INFORMATION FOR SEQ ID NO: 5:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE:
        (A) DESCRIPTION: polypeptide (vi) ORIGINAL SOURCE:
        (A) ORGANISM: Glossina morsitans morsitans
        (B) INDIVIDUAL ISOLATE: adult salivary glands (vii) IMMEDIATE SOURCE:
        (A) LIBRARY: construct from native RNA
        (D) CLONE: TTI-positive (ix) FEATURE:
        (A) NAME/KEY: putative TTI cDNA polypeptide
        (D) OTHER INFORMATION:  residues after a stop codon
            corresponding to position 51 of SEQ ID NO: 2

(xi) SEQUENCE DESCRIPTION: SEQ ID NO:5:

Phe Ser Thr Arg Arg Arg Ile Asp
                5

(2) INFORMATION FOR SEQ ID NO: 6:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE:
        (A) DESCRIPTION: polypeptide (vi) ORIGINAL SOURCE:
        (A) ORGANISM: Glossina morsitans morsitans
        (B) INDIVIDUAL ISOLATE: adult salivary glands (vii) IMMEDIATE SOURCE:
        (A) LIBRARY: construct from native RNA
        (D) CLONE: TTI-positive (ix) FEATURE:
        (A) NAME/KEY: putative TTI cDNA polypeptide
        (D) OTHER INFORMATION:  residues that follow a stop codon
            corresponding to position 60 of SEQ ID NO: 2

(xi) SEQUENCE DESCRIPTION: SEQ ID NO:6:

Asp Gln Phe Val Arg Ile Cys Lys Val Arg Arg Asn Lys Cys Ile
                5                   10                  15

Lys Lys Asn Asn Ile Asp Ala Thr Lys Lys Lys Lys Lys
                20                  25
```